United States Patent
Ranftl et al.

(10) Patent No.: US 9,568,342 B2
(45) Date of Patent: Feb. 14, 2017

(54) SENSOR COMPONENT HOUSING

(71) Applicant: Schott AG, Mainz (DE)

(72) Inventors: Reinhard Ranftl, Pfeffenhausen (DE); Helmut Hartl, Vienna (AT)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 14/081,060

(22) Filed: Nov. 15, 2013

(65) Prior Publication Data

US 2014/0069187 A1 Mar. 13, 2014

Related U.S. Application Data

(63) Continuation of application No. PCT/EP2012/002033, filed on May 11, 2012.

(30) Foreign Application Priority Data

May 16, 2011 (DE) .................. 10 2011 101 503

(51) Int. Cl.
| | | |
|---|---|---|
| G01N 27/07 | (2006.01) | |
| G01N 33/28 | (2006.01) | |
| G01D 11/24 | (2006.01) | |
| G01K 13/02 | (2006.01) | |
| G01N 27/22 | (2006.01) | |

(52) U.S. Cl.
CPC ............ G01D 11/245 (2013.01); G01K 13/02 (2013.01); G01N 27/07 (2013.01); G01N 27/226 (2013.01); *G01K 2205/04* (2013.01); *G01N 33/28* (2013.01); *Y10T 29/49826* (2015.01)

(58) Field of Classification Search
CPC ................. G01N 27/07; G01N 33/28
USPC ............................................. 73/431
See application file for complete search history.

(56) References Cited

U.S. PATENT DOCUMENTS

| | | | |
|---|---|---|---|
| 3,995,962 A | | 12/1976 | Mylaeus |
| 4,939,468 A | * | 7/1990 | Takeuchi ............... G01N 27/24 324/663 |
| 5,124,655 A | * | 6/1992 | Takeuchi ........... G01N 33/2852 324/663 |
| 5,367,264 A | | 11/1994 | Brabetz |
| 5,857,255 A | | 1/1999 | Wichmann |
| 6,208,128 B1 | | 3/2001 | Braconnier et al. |
| 7,191,505 B2 | * | 3/2007 | Hartl et al. ................... 29/432.2 |

(Continued)

FOREIGN PATENT DOCUMENTS

| | | |
|---|---|---|
| CH | 619 162 A5 | 9/1980 |
| DE | 1 124 314 | 2/1962 |

(Continued)

OTHER PUBLICATIONS

International Search Report dated Jul. 24, 2012 for International Application No. PCT/EP2012/002033 (4 pages).

(Continued)

*Primary Examiner* — Lisa Caputo
*Assistant Examiner* — Jamel Williams
(74) *Attorney, Agent, or Firm* — Taylor IP, P.C.

(57) ABSTRACT

A sensor component housing includes at least one tube section with a tube wall, wherein the tube wall has an opening and the tube section has a diameter and a first and second end. The first and/or the second end has tilted areas such that the diameter tapers to an end diameter toward the first and/or the second end of the tube section.

14 Claims, 3 Drawing Sheets

(56) References Cited

U.S. PATENT DOCUMENTS

| | | |
|---|---|---|
| 8,207,446 B2 * | 6/2012 | Swift et al. ............... 174/110 R |
| 8,434,361 B2 * | 5/2013 | Fink ............................... 73/431 |
| 8,850,869 B2 * | 10/2014 | Hartl ........................... 73/31.05 |
| 2005/0121323 A1 | 6/2005 | Hartl et al. |
| 2009/0008250 A1 | 1/2009 | Hartl |
| 2009/0065671 A1 | 3/2009 | Burgstaller |
| 2010/0186501 A1 | 7/2010 | Fink |

FOREIGN PATENT DOCUMENTS

| | | |
|---|---|---|
| DE | 1 269 986 | 6/1968 |
| DE | 124 365 | 2/1977 |
| DE | 699 17 827 T2 | 7/2005 |
| JP | H-4-66571 A | 3/1992 |
| WO | 2009/021698 A2 | 2/2009 |

OTHER PUBLICATIONS

Notice of the Transmission of International Preliminary Report on Patentability dated Oct. 1, 2013 for International Application No. PCT/EP2012/002033 (13 pages).

\* cited by examiner

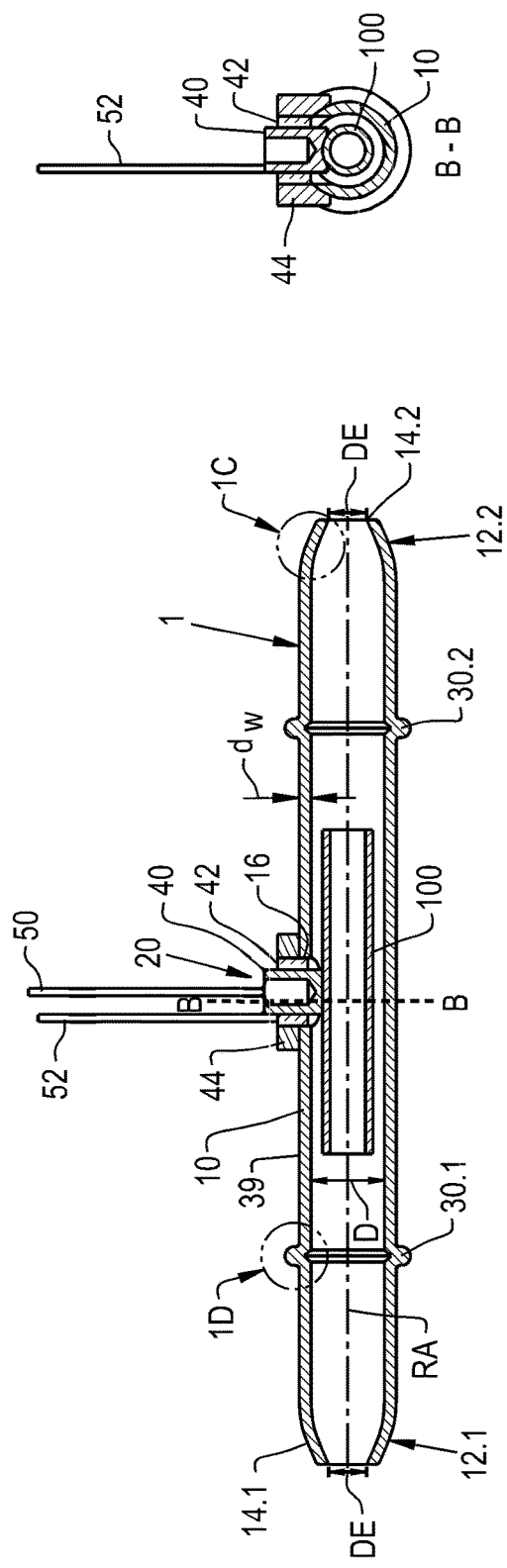

SENSOR COMPONENT HOUSING

CROSS REFERENCE TO RELATED APPLICATIONS

This is a continuation of PCT application No. PCT/EP2012/002033, entitled "SENSOR COMPONENT HOUSING", filed May 11, 2012, which is incorporated herein by reference.

BACKGROUND OF THE INVENTION

1. Field of the Invention

The present invention relates to a sensor component housing including a tube section with a tube wall, as well as a method to produce a sensor component housing and a device to accommodate and/or conduct a fluid or gaseous medium with a sensor component housing.

2. Description of the Related Art

In the current state of the art different types of sensors, for example temperature sensors are used to detect the characteristics of a medium, for example a fluid or a gas. The mediums whose physical properties, for example the temperature, are to be sensed are conducted, for example, in a line system or stored in a container, for example a tank.

To quickly capture the physical properties, for example the temperature, the sensors were hitherto arranged on the side of the feedthrough which is located near the medium, in other words near the fluid or respectively the gas.

A sensor which is arranged in this way is exposed to the medium, in other words the fluid or respectively the gas. If the system is one wherein a certain pressure is built up, then the sensors are also exposed to the pressures. An arrangement of this type is particularly problematic if the mediums are aggressive mediums, for example acids and/or if there are high pressures in the system. In such a case in a so-called arrangement of the sensors on the medium side of the feedthrough, expensive special sensors must be used.

An additional disadvantage of sensors located on the medium side can be found in that in the event of defects, sensors arranged in this manner can only be accessed with difficulty or not at all. Calibration is also only possible with great effort.

Alternatively to an arrangement of the sensors on the medium side, sensors, for example temperature sensors, can also be arranged on the outside wall of a container, for example a tank or a line. In an arrangement outside the medium there is however the problem of measurement inaccuracies. An additional problem is that when a sensor is arranged on the outside wall of, for example, the line or the tank, temperature changes cannot be detected accurately. One reason for this is the large thermal mass of the line or respectively the tank which leads to a considerable sluggishness and does not allow detection of rapid temperature changes.

Instead of an arrangement on the outside wall of the line or respectively the tank, the sensors can also be placed in the line in a special sensor housing, whereby the sensor in the sensor housing is arranged on the side facing away from the medium. An arrangement of this type is described for example in U.S. Pat. No. 5,367,264. The sensor known from U.S. Pat. No. 5,367,264 essentially serves to determine the volumetric proportion of one substance in a mixture of two substances. From U.S. Pat. No. 5,367,264 one sensor in particular has become known with which a temperature of a flowing medium or respectively its entire composition can be measured in a tube.

An additional sensor is known from US Patent Application Publication No. 2005/0121323A1 with which the concentration of additives or contaminations in oil can be determined. The sensor according to US Patent Application Publication No. 2005/0121323A1 includes a housing component which is connected with a line in such a way that an electrode is accommodated by the housing component hermetically sealed. A temperature measurement is not disclosed in US Patent Application Publication No. 2005/0121323A1; also no other types of sensors.

A device with a sensor component has become known from US Patent Application Publication No. 2010/0186501 A1 which comprises a tubular sensor component housing. The sensor component housing has a tube wall and at least one opening introduced into the tube wall, into which a feedthrough for a sensor component can be inserted. An interior tube embedded into the sensor housing component is used in particular as the sensor component. If the sensor housing component in its embodiment of outside tube is connected to a potential and the interior tube in the embodiment of the sensor component is connected to another potential then a capacitance measurement can be conducted which provides information in regard to the composition of the medium passing through the sensor component.

The sensor component housing according to US Patent Application Publication No. 2010/0186501 is manufactured from a round blank by means of machining, for example turning or milling. Producing the sensor component housing according to US Patent Application Publication No. 2010/0186501 A1 by means of a turning or milling process is however very expensive. Moreover, there are high material losses of up to 75% from blank to finished part. The arrangement of the tube ends and, in particular, their connection for example to fuel lines is also problematic.

What is needed in the art is a sensor component housing, for example for a device with a sensor component, with which the previously described disadvantages of the current state of the art, in particular in the form of US Patent Application Publication No. 2010/0186501A1 can be overcome. A sensor component housing is to be specified, for example, which requires minimal production costs and which can be securely connected at the ends, for example to a line, such as a fuel line.

SUMMARY OF THE INVENTION

The present invention provides a sensor component housing which includes a tube section with a tube wall, whereby the tube wall has an opening and the tube section has a diameter and a first and a second end. It is moreover provided that the first and/or second end includes tilts which were produced in a production process which includes a reshaping step, so that the diameter tapers towards the first and/or second end of the tube section. An arrangement of this type with a tilt allows for the inventive sensor component housing to be inserted in the simplest manner in a line system, for example in a fuel line, whereby the seal of the transition from the line to the sensor housing component is ensured due to the tilt.

A feedthrough for a sensor component, for example an interior tube for a capacitance measurement as described in detail in US Patent Application Publication No. 2010/0186501 A1 is, for example guided through the opening of the sensor component housing. The disclosure content of US Patent Application Publication No. 2010/0186501 A1 is incorporated herein in its entirety.

In accordance with one embodiment of the present invention, the feedthrough is guided through the opening. The feedthrough may include a reinforcing component, whereby the reinforcing component is connected with the sensor component housing using of brazing.

The feedthrough can be multi-component and include a cup, a glass or glass ceramic material and a component, for example a reinforcing component.

Use of a reinforcing component has the advantage that different materials can be used for the sensor component housing and the reinforcing component. The materials for the sensor component housing and for the reinforcing component may be selected to be different in such a way that the materials are adapted and are compatible with each other. The sensor component housing may, for example, be adapted to the medium flowing through the sensor component housing, such as to the medium which is to be detected.

In contrast, the reinforcing component can include a material which is of high strength. The material for the reinforcing component consists, for example of a corrosion resistant material and is adapted to a stable, secure optimum glazed seal. Additionally, a relatively thin-walled raw material can be used for the sensor component housing which, compared to the current state of the art leads to material savings, since removal of the excess material through turning or milling as described, for example, in US Patent Application Publication No. 2010/0186501 is not necessary. The greater wall thickness that is required in the region of the feedthrough for the sensor component is provided, for example by the reinforcing component.

Pushing the lines which are connected at the tilted ends too far is prevented, for example, by thickening provided on the tube walls of the sensor component housing. In practical terms the thickenings serve as a stop for the connection lines which were pushed beyond the tilt onto the sensor component housing.

Producing the tilt involves a shaping process, for example shaping through compression. Production may occur by shaping alone, for example through compression, or shaping is accomplished after a process such as for example chamfering through milling. However, the cost of production by shaping alone compared to the current state of the art can hereby be reduced. The shaping process changes the material in its density. In particular, a section through the component illustrates the production process.

If the component is produced by a machining process, for example turning, according to the current state of the art, then the structural-/flow lines extend substantially parallel and point in the same direction. If the shape of the component is obtained by compression or respectively shaping, in other words if the tilt is produced by a shaping process, then the structural lines are bent by the shaping process. Conclusions can be reached in regard to the production process based on a metallurgic section.

Due to the fact that the lines of force are bent in the component after shaping, the rigidity in the component is increased resulting in that damage of the sensor component in the region of the thus produced tilt is avoided more reliably compared to the current state of the art, for example when pushing the fuel lines onto the sensor component.

Exemplary materials used for the sensor component housing are steel, such as standard steel, for example St35, St37, St38 as well as high grade steel or stainless steel due to their high corrosion resistance, or NiFeCo-alloys or respectively NiFe-alloys or a combination of the aforementioned materials. High grade steels, due to the excellent corrosion resistance of the material, are feasible whereby no additional plating process is required.

In addition to the sensor component housing the present invention also provides a method for the production of such a sensor component housing which provides for an especially simple manufacturability compared to the method for the production of a sensor component housing by means of a turning or milling process as described in US Patent Application Publication No. 2010/0186501 A1.

The method according to the current invention provides a tube section having a tube wall. The tube section is obtained, for example through cutting from a welded tube or also a seam-free tube. The tube has a tube wall having a wall thickness in the range of between approximately 0.3 millimeters (mm) and 1.5 mm, for example between 0.5 mm and 1.0 mm. The upper limit of the wall thickness of approximately 1.3 mm is limited in that thicker walls can only be processed with difficulty through shaping technology. In particular, the expenditure of force for a shaping process, for example compression becomes too great. The lower limit of the tube thickness of, for example 0.3 mm, is limited in that tubes which have insufficient wall thickness do not have sufficient rigidity for shaping processes and can bend or tear out.

An opening produced through punching is introduced into the tube wall, for example for the feedthrough of the sensor component and a taper is produced by simple shaping at the first and/or second end of the tube section, whereby the diameter of the tube section reduces in the region of the first or second end. The shaping process is basically a compression process with which the tilt is produced through tapering. With the method according to the present invention great material cost savings can be achieved and a cost effective production can be realized. Moreover the tilt at the tube ends can be produced in a simple manner through shaping. Due to the tilt at the tube end it is possible to connect the sensor component housing to a conventional fuel line without causing damage to seals, for example O-ring seals of the connecting piece or connectors of the fuel line. Due to the tilt according to the present invention, leaks in the region where the fuel line connects to the inventive sensor component housing are therefore avoided.

In order to avoid pushing the lines which are connected to the sensor component too far it, the tube wall may again be provided with a thickening which is produced through shaping, such as compression.

A feedthrough, for example for a sensor component located in the sensor component housing, for example an inside tube may be inserted into the opening and be connected in a simple manner by brazing with the sensor component housing.

In addition to the sensor housing component and the method to produce same, the present invention also relates to a device to accommodate and/or convey a fluid or gaseous medium, with a sensor component and a sensor component housing according to the present invention. This device is characterized in that it includes an inventive sensor component housing with a tilt for improved connection to the fuel line. In the device with the sensor component housing according to the present invention, the sensor component is centered in the housing in that centering of the sensor component, which for example is tube shaped, occurs through the outside diameter of the tube-shaped sensor component housing.

In contrast thereto centering in the device according to US Patent Application Publication No. 2010/0186501 A1 occurs through the inside diameter of the outside tube, in this case the sensor component housing. With this type of centering however, a tilt could not be produced, since centering with a tilt is very difficult for centering of this type.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIGS. 1a-1d illustrate a device with a sensor component housing according to the present invention, along with a feedthrough as well as a sensor component in the embodiment of a tube shape, located in the sensor component housing;

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

Figure 2:
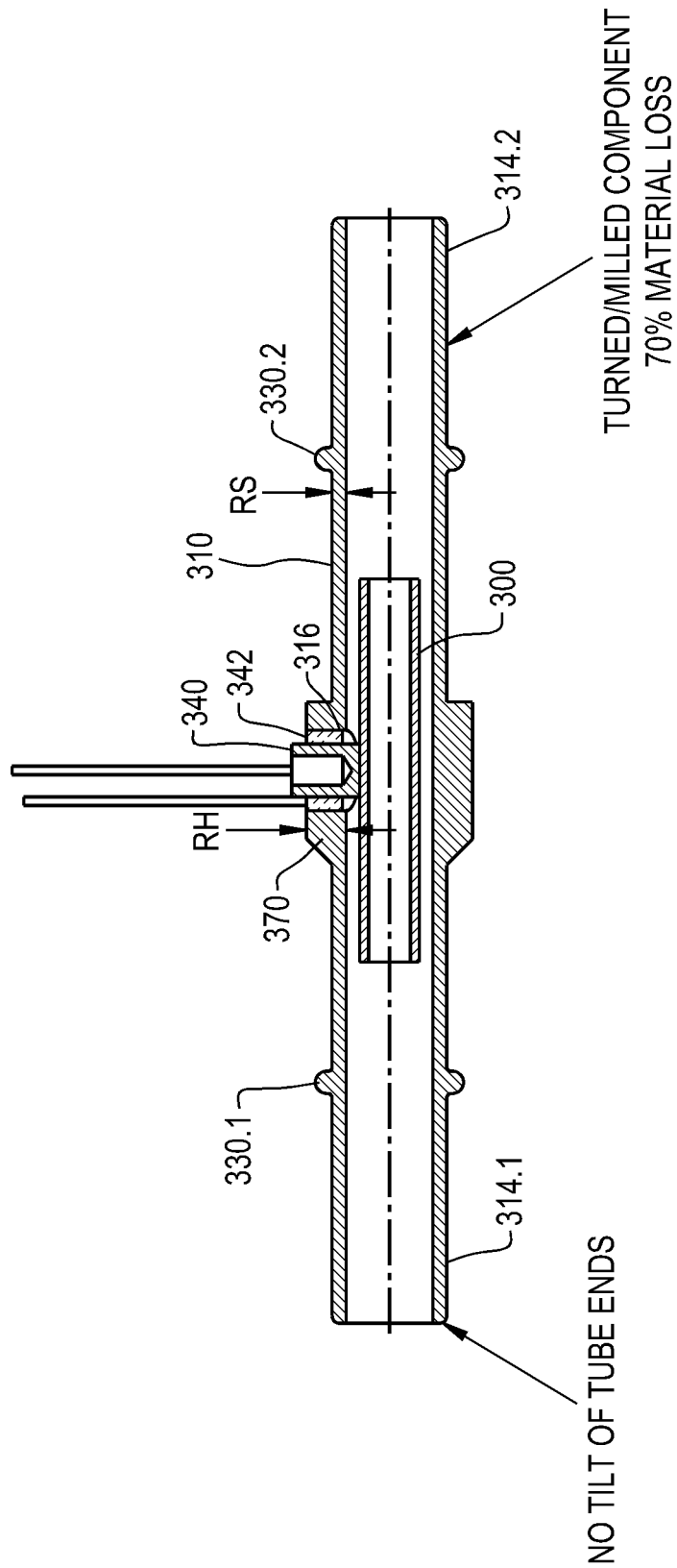
FIG. 2 illustrates a device according to the current state of the art.

Referring now to FIGS. 1a to 1d, there is shown a device to accommodate and/or conduct a fluid or gaseous medium, with a sensor component 100 which is embedded in a sensor component housing 10 according to the present invention. FIG. 1a illustrates a longitudinal section through such a device 1. Sensor component housing 10 has a circular cross section which is illustrated in plane B-B in FIG. 1b.

The diameter of the circular tube cross section is D. The present invention provides that sensor component housing 10 has a tilt 14.1 or respectively 14.2 in the region of first end 12.1, as well as second end 12.2. Tilt 12.2 is illustrated in more detail in FIG. 1c. At the tilt, the first end 12.1 or respectively second end 12.2 of the tube section of sensor housing component 10 is compressed, for example with a shaping tool and the diameter is reduced from diameter D in the region of the tube center to diameter DE at the tube end 12.1, 12.2. Even though in the current example diameter DE on first end 12.1 is consistent with diameter DE on second end 12.2 this is not mandatory. Different diameters are also possible.

The wall thickness of tube wall 39 is $d_w$. The thickness of tube wall 39 is, for example in the range of between approximately 0.3 mm and 1.5 mm.

In the current embodiment of the present invention, an opening 16 is worked into tube wall 39 with a wall thickness $d_w$ of sensor component housing 10 which is, for example, produced through punching through the wall thickness $d_w$ of tube wall 39. In the current embodiment of the present invention a glass-metal feedthrough 20 is inserted into opening 16 which is produced through punching. The glass-metal feedthrough includes a housing component which, in the current example, however not exclusively, is in the embodiment of a cup 40 as described for example in US Patent Application Publication No. 2010/0186501 A1, the disclosure content of which is incorporated hereon in its entirety. Cup 40 is, for example, a metal part which is sealed/embedded in glass into opening 16 in tube wall 39. The glass material between cup 40 and opening 16 is identified with 42. Since wall thickness $d_w$ of the tube is not sufficient to make the seal, the feedthrough according to the present invention includes in accordance with an embodiment of the present invention a component which is placed on tube wall 39, for example a reinforcing component 44. Reinforcing component 44 can be of the same material as tube wall 39, but does however not have to be.

The material for the sensor component may be selected so that it is compatible with the medium flowing through the sensor component housing or the medium which is to be detected. The material of the reinforcing component is adapted to a stable, reliable and optimum seal with glass or respectively glass ceramic material 42. The additional component, for example reinforcing component 44 is connected with tube wall 39, for example through brazing. A first line 50, for example for a temperature sensor (not illustrated), is inserted into cup 40 which is embedded in glass in the feedthrough. Cup 40 of the feedthrough is in turn conductively connected with sensor component 100 in the embodiment of an inside tube as described in US Patent Application Publication No. 2010/0186501 A1. Cup 40 is connected with line 52 which can be connected to a potential. Between tube wall 39 of the sensor component housing and the inside tube a potential difference or respectively a voltage can then be applied, if tube wall 39 is for example grounded and cup 40 and thereby inside tube 100 are connected to potential. The potential difference between outside tube and inside tube is the basis for a capacitance measurement of fluid or gas flowing through the inside tube. From the capacitance values or respectively the changes of the capacitance values conclusions can be made as to what material or respectively medium is flowing through tube shaped sensor component 100. Due to the embodiment of sensor component 100 as an inside tube with parallel surfaces to the outside tube, the capacity surfaces are greatly enlarged and capacitance measurements of medium flowing in tube shaped sensor sections improved. The following mediums which can be measured with the assistance of the device illustrated in FIG. 1a are conceivable: natural gas, hydrogen, nitrogen, oxygen, exhausts from combustion engines, industrial process gasses, liquid petroleum gas, air, water, such as salt water, oils, for example for engines, transmission and hydraulic applications, alcohols, such as methanol and ethanol, gasoline, diesel fuel, rapeseed oil, methyl ester, fuel for aircraft turbines, urea and urea solutions, and hydrofluorocarbons.

In order to avoid pushing the fuel lines which are connected to first and second end 12.1, 12.2 too far, tube wall 39 of the tube of the sensor component housing has a continuous thickening 30.1, 30.2. The continuous thickening 30.1 is illustrated in more detail in FIG. 1d.

As can be seen in FIG. 1d, the thickening can also be produced very simply through compression of the tube wall by maintaining the tube diameter. FIG. 1b is a cross section through a device according to FIG. 1a along line B-B.

Clearly visible is line 52 which is connected conductively to cup 40, which in turn is connected with the sensor component in the embodiment of inside tube, so that a potential can be connected to sensor component 100. Cup 40 of the feedthrough is sealed embedded in a glass material 42 into the opening and the additional component or respectively reinforcing component 44 placed on the opening. Line 52 is thereby separated electrically from tube wall 10. Tube wall 10 may for example be grounded so that no capacitance measurement between sensor component 100 in the embodiment of inside tube and sensor component housing 10 in tube shape, in other words the outside tube 10 is possible.

FIG. 2 illustrates one design form of a tube-shaped device to accommodate and conduct gaseous or fluid medium, with a sensor component housing 310 and a sensor component 300 according to the current state of the art, as described in US Patent Application Publication No. 2010/0186501 A1, the disclosure content of which is incorporated herein in its entirety. Same components as in FIGS. 1a-1d are identified by reference numbers which are increased by 200.

In contrast to the arrangement according to FIGS. 1a-1d the sensor component housing is milled and turned from one piece in the current state of the art. Cup 340 which is connected conductively with inside tube 300 in the embodiment of a sensor component is sealed embedded in glass into an opening 316 in the tube wall. Glass material 342 is thereby in direct contact between raised section 370 of the tube wall and cup 340. The glass seal is identified with reference number 342. The thickness of the tube wall is RS, the thickness of raised section 370 is RH. In the current example the thickness of tube wall RS is less than that of raised section 370. This is achieved in that a tube having thickness RS is produced for the tube wall from a blank having thickness RH by means of a machining process which is expensive and connected with high material use. As a result of the machining process, thickenings 330.1, 330.2 are provided on the tube wall of sensor component housing 310. In contrast to the present invention no tilts which extend over a longer section may be provided at ends 314.1, 314.2 of sensor housing component 310, due to which no tight connection of a connecting line, for example a fluid, such as a fuel line is possible. Through direct sealing in glass into the tube wall the device according to FIG. 2 is also characterized in that cup 340 is in direct contact with inside tube 300 in the embodiment of sensor component. Inside tube 300 has a very thin wall thickness, for example a wall thickness in the range of between approximately 0.3 mm to 1.0 mm. Inside tube 300 which is connected with the sensor section extends over at least half the length L of sensor component housing 310 which is in the embodiment of a tube. By introducing inside tube 300 various advantages can be achieved. The inside tube ensures that a laminar flow is present in the tube-shaped sensor component and that no flow deterioration occurs. Moreover, heat surfaces which are in direct contact with a temperature sensor which is arranged in the cup (not illustrated) are substantially expanded or enlarged. This in turn improves the accuracy of temperature measurements of mediums which flow through the tube-shaped sensor component. For a capacitance measurement the outside tube is connected to a potential and the inside tube to another potential. In this way it is possible to conduct a capacitance measurement which provides conclusions in regard to the composition of the medium passing through the device. Based on the configuration of the inside tube with parallel surfaces, the capacitive surfaces are greatly enlarged and the capacitance measurement of flowing medium in the device improved. The dimensions of the inside tube as described in the current state of the art may also be selected for sensor component 100 in the embodiment of an inside tube with its previously described advantages, utilized in the present invention (in FIGS. 1a-1d).

Figure 3A:
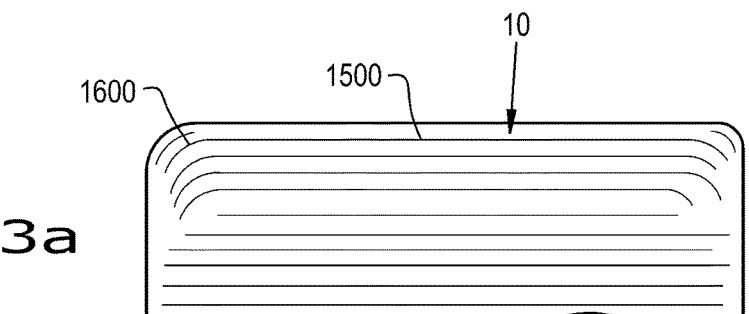
FIGS. 3a-3b illustrates a metallurgic section through a component or respectively part of a component according to the present invention produced through a shaping process.
Figure 3B:
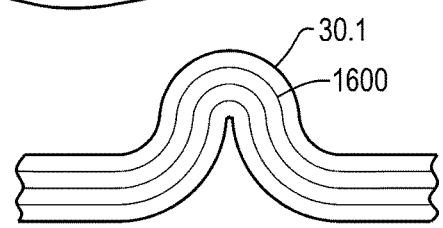

Referring now to FIGS. 3a-3b, there is shown schematic diagrams of a metallurgic cut through a section of a component according to the present invention which was produced in a shaping process, as illustrated in FIGS. 1a-1d. The schematic diagrams are not to scale and are only intended to illustrate in principle the progression of flow lines in the case of a shaped component. Same components as illustrated in FIGS. 1a-1d are identified with the same reference numbers.

As can be seen in the metallurgic cut according to FIGS. 3a-3b, components produced according to the inventive process are identified by structural-/flow lines 1500 which were bent in region 1600 during the shaping process. Especially prominent is the bending of the structural-/flow lines for the continuous thickening 30.1, 30.2 as shown in FIG. 3b which are bent in region 1600 during the shaping process.

Figure 4A:
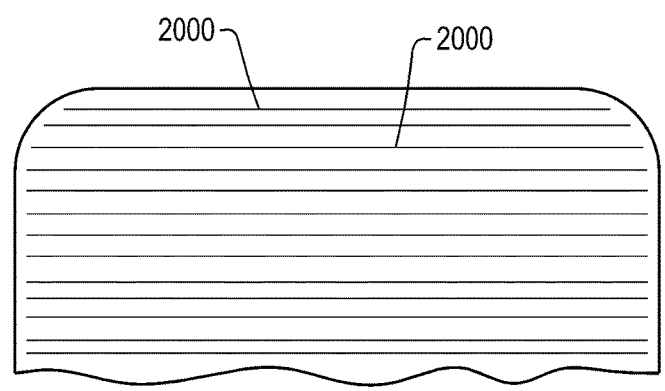
FIGS. 4a-4b illustrate a metallurgic section through a component or respectively part of a component, produced through a machining process.
Figure 4B:
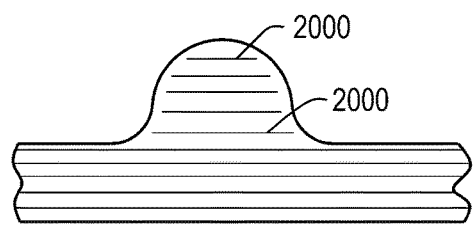

In contrast thereto, FIGS. 4a-4b are schematic diagrams of a metallurgic cut of a component 300 produced by means of machining in accordance with US Patent Application Publication No. 2010/0186501 A1 which in particular is a turned component. Structural-/flow lines 2000 are again shown. Structural-/flow lines 2000 are substantially parallel and point in the same direction. This schematic diagram is also not to scale and is intended only to illustrate in principle the progression of flow lines for a component produced by means of turning and milling. Especially clear is again the difference in the progression of the structural-/flow lines 2000 in the region of a thickening according to FIG. 4b. The difference to the shaped component according to FIG. 3b is clear.

The present invention provides for the first time a simple sensor component housing which can be produced with less material loss compared to the current state of the art specified in US Patent Application Publication No. 2010/0186501 A1, and a device to determine the composition of fluid or gaseous medium which is conducted through a tube shaped sensor component housing which is equipped with a sensor component. The tilt in particular which is produced in a simple manner which includes at least one shaping process permits a tight connection to fluid—in particular fuel lines. By producing the tilt with the assistance of a shaping process, considerable material savings can be achieved compared, for example, to machining alone. The component produced by a method which includes at least one shaping process has bent structural-/flow lines due to the shaping process, in contrast to parallel progressing flow lines of components produced according to machining processes of the related art. A shaped component can hereby have greater stiffness in the region of the tilt than a component produced through machining, whereby material damage, for example when pushing a fuel line onto the taper, can be avoided. An additional advantage of the present invention can be found in that in an embodiment of the present invention the sensor component housing and the reinforcing component can be produced from different materials, whereby the material of the sensor component housing is adapted to the medium which is to be detected and the material of the reinforcing component is adapted to a stable, secure and optimum glazed seal.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A sensor component housing, comprising:
at least one tube section having a diameter and at least one thickening formed by a shaping process, a first end and a second end and a tube wall having an opening, said tube section defining an interior volume bounded by at least one interior surface of said tube wall, at least one of said first end and said second end having a tilt such that said diameter of said at least one tube section tapers towards at least one of said first end and said second of said tube section to an end diameter, said tilt having been shaped, said opening being at least one opening configured to accommodate a feedthrough for a sensor component, said feedthrough for said sensor component being connected with said tube wall through one of a soldered connection and a welded connection, said at least one opening accommodating said feedthrough for said sensor component further comprising a reinforcing component surrounding said at least one opening and being connected with at least one exterior surface of said tube wall through one of a soldered connection and a welded connection such that said reinforcing component does not contact said at least one interior surface of said tube wall.

2. The sensor component housing according to claim 1, wherein said tilt has been compressed.

3. The sensor component housing according to claim 1, wherein said reinforcing component is formed of a material compatible with a stable and optimum glazed seal with said glass material or said glass ceramic material.

4. The sensor component housing according to claim 1, said sensor component being a tube section.

5. The sensor component housing according to claim 4, said sensor component being an inside tube for one of a capacitance measurement and an optical sensor.

6. The sensor component housing according to claim 1, wherein the sensor component housing is at least one of:
selected to be compatible with a medium which flows through the sensor component or said medium to be detected; and
the sensor component housing includes at least one of steel, a high grade steel, a Nickel-Iron-Cobalt (NiFeCo) alloy and a Nickel-Iron (NiFe) alloy.

7. A method to produce a sensor component housing, the method comprising the steps of:
providing a tube section having a diameter and a tube wall, said tube section defining an interior volume bounded by at least one interior surface of said tube wall;
introducing at least one opening into said tube wall;
surrounding said opening with a reinforcing component which is connected with at least one exterior surface of said tube wall such that said reinforcing component does not contact said at least one interior surface of said tube wall;
producing a tilt by shaping at least one of a first end and a second end of said tube section such that said diameter of said tube section is reduced; and
providing said tube wall with a thickening having material with bent flow lines.

8. The method according to claim 7, wherein said at least one opening is introduced into said tube wall through punching.

9. The method according to claim 7, said thickening being provided through compression.

10. The method according to claim 7, further comprising the step of connecting a feedthrough for a sensor component with said tube wall.

11. A device for at least one of accommodating and conducting a fluid or gaseous medium, the device comprising:
a sensor component housing including at least one tube section having a diameter and at least one thickening formed by a shaping process, a first end and a second end and a tube wall having an opening, said tube section defining an interior volume bounded by at least one interior surface of said tube wall, at least one of said first end and said second end having a tilt such that said diameter of said at least one tube section tapers towards at least one of said first end and said second of said tube section to an end diameter, said tilt having been shaped; and
a sensor component compatible with the fluid or gaseous medium and including a feedthrough, the fluid or gaseous medium being one of natural gas, hydrogen, nitrogen, oxygen, exhaust from combustion engines, industrial process gasses, liquid petroleum gas, air, water, oils, alcohols, gasoline, diesel fuel, rapeseed oil, methyl ester, fuel for aircraft turbines, urea, urea solutions, and hydrofluorocarbons, said opening being at least one opening accommodating said feedthrough, said feedthrough being connected with said tube wall through one of a soldered connection and a welded connection, said at least one opening accommodating said feedthrough further comprising a reinforcing component surrounding said at least one opening and being connected with at least one exterior surface of said tube wall through one of a soldered connection and a welded connection such that said reinforcing component does not contact said at least one interior surface of said tube wall.

12. The device according to claim 11, said water being salt water.

13. The device according to claim 12, said oils being for at least one of engines, transmission and hydraulic applications.

14. The device according to claim 13, said alcohol being one of methanol and ethanol.

* * * * *